(12) United States Patent
Ghannoum et al.

(10) Patent No.: US 9,987,316 B2
(45) Date of Patent: Jun. 5, 2018

(54) PROBIOTIC CONTROLLING FUNGI AND USES THEREOF

(71) Applicant: Case Western Reserve University, Cleveland, OH (US)

(72) Inventors: Mahmoud A. Ghannoum, Cleveland, OH (US); Pranab Mukherjee, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days. days.

(21) Appl. No.: 14/028,057

(22) Filed: Sep. 16, 2013

(65) Prior Publication Data

US 2014/0186318 A1 Jul. 3, 2014

Related U.S. Application Data

(60) Provisional application No. 61/701,275, filed on Sep. 14, 2012.

(51) Int. Cl.
*A61K 36/064* (2006.01)
*A61K 36/062* (2006.01)

(52) U.S. Cl.
CPC .................................. *A61K 36/062* (2013.01)

(58) Field of Classification Search
None
See application file for complete search history.

(56) References Cited

U.S. PATENT DOCUMENTS

| 2008/0260709 A1* | 10/2008 | Sawada et al. ............ 424/93.51 |
| 2010/0111927 A1 | 5/2010 | Kim |
| 2010/0159006 A1* | 6/2010 | Schmidtchen ....... C07K 5/0812 514/1.1 |
| 2012/0201798 A1 | 8/2012 | Kekkonen et al. |
| 2013/0011344 A1 | 1/2013 | Segura et al. |
| 2013/0224254 A1 | 8/2013 | Petit et al. |

FOREIGN PATENT DOCUMENTS

WO    WO 2008054293 A1 *  5/2008  ........... A61K 31/375

* cited by examiner

*Primary Examiner* — Robert J Yamasaki
(74) *Attorney, Agent, or Firm* — Tarolli, Sundheim, Covell & Tummino LLP

(57) ABSTRACT

A method for controlling detrimental oral organisms in various individuals includes administering a priobiotic composition that includes one or more species or strains of beneficial fungi and/or one or more compounds produced therefrom that control one or more species of detrimental oral bacteria and/or other organisms.

4 Claims, 5 Drawing Sheets

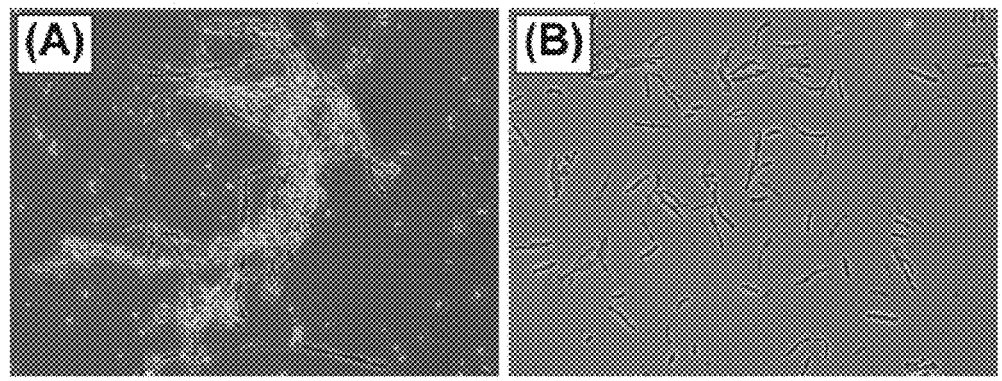
Figs. 5A-B
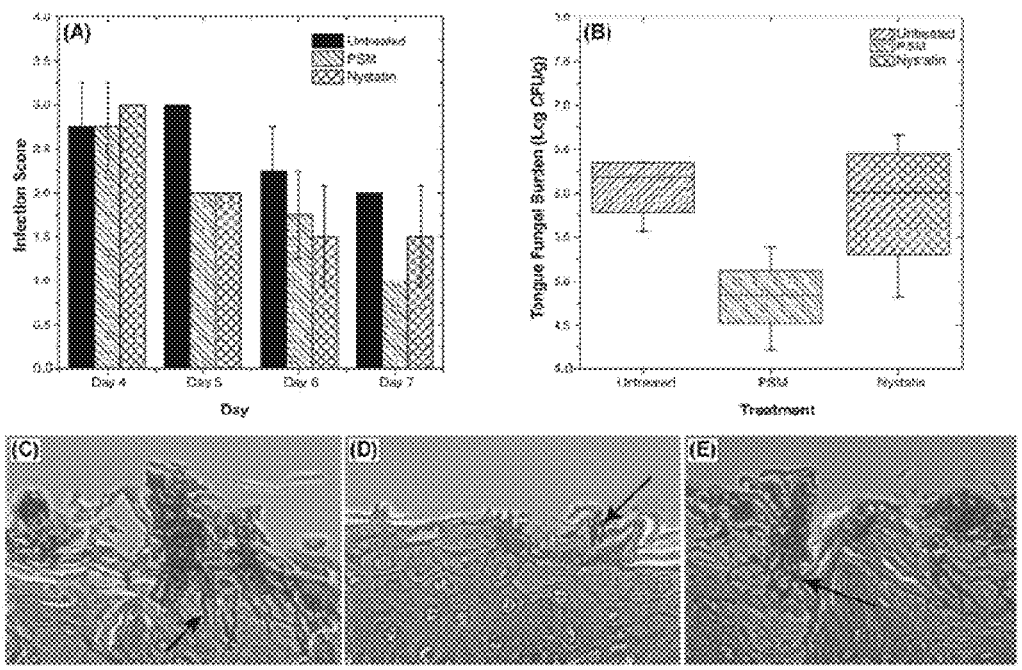
Fig. 6

PROBIOTIC CONTROLLING FUNGI AND USES THEREOF

RELATED APPLICATION

This application claims priority from U.S. Provisional Application No. 61/701,275, filed Sep. 14, 2012, the subject matter of which is incorporated herein by reference in its entirety.

TECHNICAL FIELD

The present invention relates to priobiotic compositions and methods for the utilization of the same to control detrimental oral organisms in a subject in need thereof, and, more particularly, to control detrimental oral organisms present in both healthy and immune-compromised (e.g., HIV-positive individuals, organ transplant patients, etc.) individuals.

BACKGROUND

Organisms comprising the oral microbiota contribute to health and disease, and their disruption may indicate, trigger, or influence the course of oral diseases like oral candidiasis. To date, studies of the oral microbiota have primarily focused on bacteria, especially in disease settings.

Organisms residing in the oral cavity (oral microbiota) contribute to health and disease, and influence oral diseases like oral candidiasis (see, e.g., Jenkinson, H. F., et al.; Oral Microbial Communities in Sickness and in Health; Trends Microbiol., Vol. 13, pp. 589 to 95, 2005), an infection caused by the fungus *Candida* (see, e.g., Nokta, M.; Oral Manifestations Associated with HIV Infection; Curro HIV/AIDS Rep. Vol. 5, pp. 5 to 12, 2008; or Patton, L. L., et al.; Prevalence and Classification of HIV-Associated Oral Lesions; Oral Dis. Vol. 8, pp. 98 to 109, 2002; or Shiboski, C. H.; HIV-Related Oral Disease Epidemiology among Women: Year 2000 Update; Oral Dis. Vol. 8, pp. 44 to 48, 2002), and the most common oral complication of HIV-infection. As has been studied and published, the pathogenesis of oral candidiasis is linked to changes in the CD4+ cell count, antiretroviral therapy (ART), and cigarette smoking in HIV-1-infected patients. Although the introduction of ART has reduced mortality and morbidity as well as the incidence of opportunistic infections including oral candidiasis among HIV-infected patients, recent studies indicate that the decline of oral candidiasis among ART-experienced HIV patients is transient in some HIV-infected individuals. In this regard, a recent study showed that in patients with advanced AIDS, oral yeast colonization was extensive, occurring in 81.1 percent of the 122 patients studied and symptomatic infection occurred in one-third. In addition, resistant yeasts were still common, occurring in 25.3 percent of patients colonized with yeasts or with symptomatic infection. Thus, oral candidiasis remains a significant disease in advanced AIDS, even in the era of ART.

Changes in the human gut microbiota have been associated with conditions like allergies, Celiac's disease, gastric cancer, obesity, anorexia and inflammatory bowel disease. The oral microbiome of the subgingival plaque in HIV-infected patients has also been characterized. However, most studies to date have focused on the bacterial component of the microbiome (bacteriome), in both oral and non-oral body sites with no attention to the mycobiome (fungal members of the oral microbiome). Recently, the oral mycobiome in healthy individuals was characterized using high-throughput multitag pyrosequencing (MTPS), and reported that humans are colonized with up to 85 fungal genera (see, e.g., Ghannoum, M. A., et al.; Characterization of the Oral 25 Fungal Microbiome (Mycobiome) in Healthy Individuals; PLoS Pathogens Vol. 6, e1000713, 2010). Although this study demonstrated the complexity of the human oral microbiome, the specific contribution of the mycobiome to diseases including HIV-infection remained elusive further investigation.

SUMMARY

Embodiments described herein relate to methods for controlling detrimental oral organisms in subjects, such as humans, and, more particularly, methods for controlling various types of detrimental oral organisms present in both healthy and immune-compromised (e.g., HIV-positive individuals, organ transplant patients, etc.) individuals.

Other embodiments relate to priobiotic compositions and methods for the utilization of same to control various unwanted or undesirable oral organisms using one or more beneficial or less deleterious organisms. Still other embodiments relate to one or more species or strains of beneficial fungi that control one or more species of detrimental oral bacteria and/or other organisms.

In some embodiments, a method for reducing *Candida* amounts in the oral cavity of an individual includes the use of at least one *Pichia* fungus.

In another embodiment, a method to control various deleterious microbiotic organisms in immune-compromised individuals (e.g., HIV-positive individuals, organ transplant patients, etc.) includes the use of one or more good, or less deleterious, microbiotic organisms and/or one or more compounds produced thereby or therefrom as shown and described herein.

BRIEF DESCRIPTION OF THE DRAWINGS

FIG. 1(A) shows the relative abundance of bacteria in uninfected and HIV-infected patients (N=11 for each group), and FIG. 1(B) shows bacteria present in the core oral bacteriome of uninfected and HIV-infected individuals.

FIG. 2(A) shows the relative abundance of fungi in uninfected and HIV-infected patients (N=12 for each group), and FIG. 2(B) shows fungi present in the core oral mycobiome of uninfected and HIV-infected individuals.

FIG. 3(A) shows the relative abundance of *Pichia* & *Candida* in uninfected individuals, FIG. 3(B) shows the effect of PSM on growth of *Candida* was determined by measuring optical density (OD), and FIGS. 3(C-D) show the effect of PSM on *Aspergillus*, and *Fusarium* as determined by measuring dry weight of fungi.

FIG. 4(A) shows the effect of *Pichia* cells on the ability of *Candida* to form biofilms. *Candida* and *Pichia* were co-incubated [*Candida:Pichia* (C:P)=3:1, 1:1, or 1:3] and biofilm formation was monitored (*P≤0.002, compared to *Candida* or *Pichia* controls). FIG. 4(B) shows the effect of media supernatant obtained from *Pichia* or *Penicillium* on *Candida* biofilms. Mean±SD of ≥3 separate experiments. FIGS. 4(C-E) show confocal microscopy images of *Candida* biofilms formed in presence of (C) no media supernatant, (D) *Penicillium* supernatant or (E) *Pichia* supernatant. FIG. 4(F) shows thickness of biofilms formed in presence of media supernatant of *Pichia* or *Penicillium*.

FIGS. 5(A-B) illustrate graphs showing the effect of *Pichia* spent medium on *Candida* germination, where FIG. 5(A) shows germination in *Candida* exposed to fetal bovine serum, and FIG. 5(B) show stunted germ tubes formed by *Candida* exposed to *Pichia* supernatant. Magnification 20×.

FIGS. 6(A-E) illustrate graphs and images showing the efficacy of *Pichia* spent medium (PSM) in an experimental murine morel of oral candidiasis. FIG. 6(A) shows the infection score and FIG. 6(B) shows the tongue fungal burden in mice infected with *Candida*. FIGS. 6(C-E) show histology analyses of tissue section of tongue from mouse infected with *Candida*, followed by (C) no treatment, (D) PSM, or (E) nystatin.

DETAILED DESCRIPTION

Figure 1:
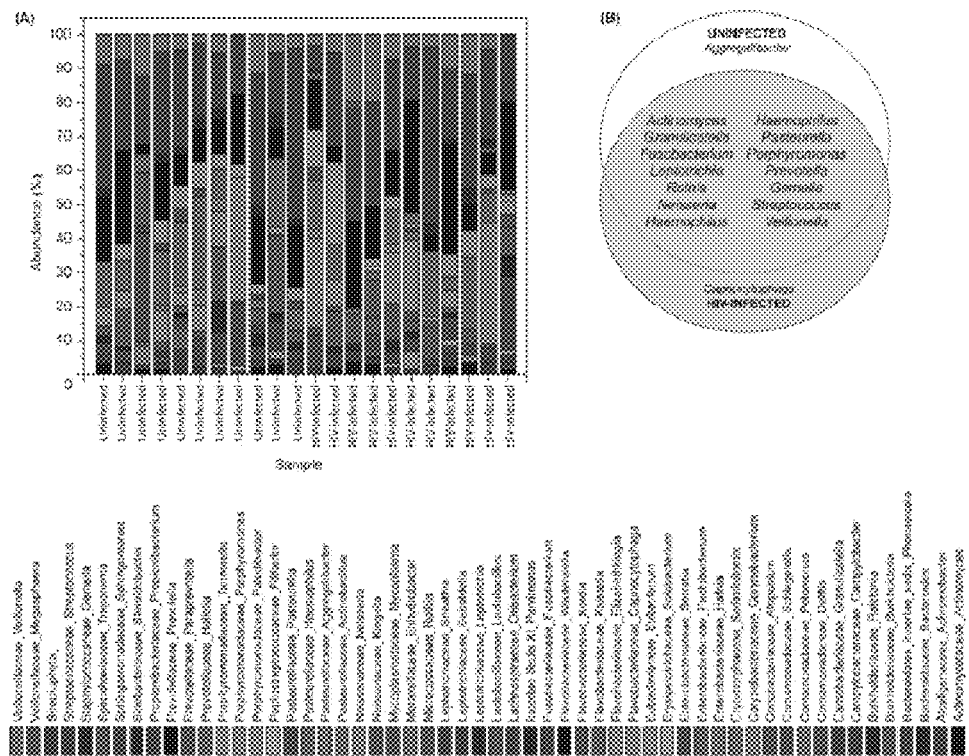
FIGS. 1(A-B) illustrate schematic drawings showing bacterial microbiome (bacteriome) of HIV-infected patients and uninfected individuals, where
Figure 2:
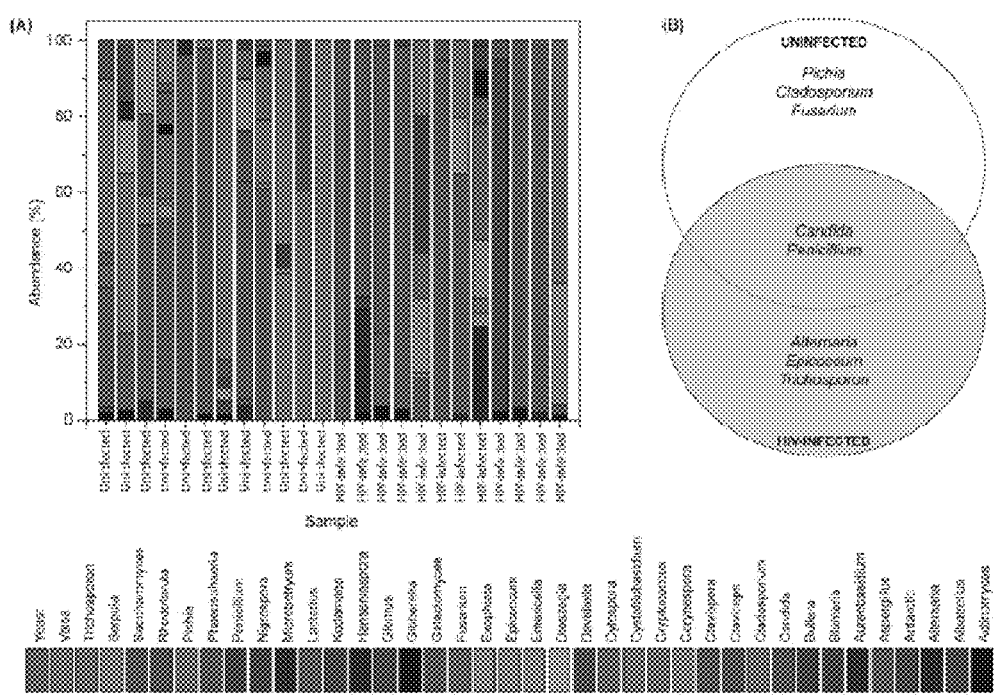
FIGS. 2(A-B) illustrate schematic drawings showing fungal microbiome (mycobiome) of HIV-infected patients and uninfected individuals, where

The term "subject" or "individual" refers to an animal, including a fowl (e.g., chickens, turkeys, and the like), and a mammal, such as a non-primate (e.g., cows, pigs, horses, cats, dogs, rats, etc.) and a primate (e.g., monkey and human), most preferably a human.

The term "topically", as opposed to "systemically", as used herein refers to an application of the compositions described herein to a definite area of the body of a subject and is interchangeably used with the term "locally." The term topically may refer to an application of the compositions described herein directly to an external area of the body, such as the oral cavity.

The term "prophylactically effective amount" as used herein refers to that amount of the composition described herein sufficient to prevent a disease or disorder associated with pathogenic microorganisms at a given site. A prophylactically effective amount may refer to the amount sufficient to prevent or suppress the growth of pathogenic microorganisms or kill pathogenic microorganisms at a given site.

The term "therapeutically effective amount" as used herein refers to that amount of the compositions described herein sufficient to treat, manage or ameliorate a disease or disorder caused by pathogenic organisms at affected sites. A therapeutically effective amount may refer to an amount of the composition sufficient to reduce the number of pathogenic microorganisms, to suppress the growth of pathogenic microorganisms (i.e., stasis), or to kill pathogenic microorganisms at the affected sites. Further, a therapeutically effective amount of the composition means that the amount of the compositions alone, or in combination with other therapies, that provides a therapeutic benefit in the treatment, management, or amelioration of a disease or disorder.

The term "probiotics" as used herein refers to viable microorganisms which alter the microflora by implantation or colonization in or onto the host, thereby exerting beneficial health effects on the host. The beneficial health effects of probiotics may be exerted particularly successfully in the environment, which is hostile to pathogenic organisms but favorable for probiotics so that the growth of the probiotics outweigh that of the pathogenic organisms.

Embodiments described herein relate to methods for controlling detrimental oral organisms in subjects, such as humans, and, more particularly, methods for controlling various types of detrimental oral organisms present in both healthy and immune-compromised (e.g., HIV-positive individuals, organ transplant patients, etc.) individuals that contribute to good oral health.

Other embodiments relate to probiotic compositions and methods for the utilization of same to control various unwanted or undesirable oral organisms using one or more beneficial or less deleterious organisms. Still other embodiments relate to one or more species or strains of beneficial fungi that control one or more species of detrimental oral bacteria and/or other organisms.

Other embodiments are directed to identifying the core oral mycobiome (COM) and bacteriome (COB) present in greater than or equal to the percent of the subjects in HIV-infected and uninfected individuals, and in identifying and demonstrating that the COM undergoes a shift in HIV disease. It was found that a decrease in abundance of the yeast *Pichia* coincided with an increase in *Candida* colonization and that there is an antagonistic relation between these two fungi. It has also been discovered herein that modulation of *Candida* virulence factors by *Pichia* is a mechanism underlying this interaction. The results contained herein provide the first evidence that a member of the oral fungal flora impact *Candida* colonization. These findings have implications regarding the management of oral candidiasis and other mucosal fungal infections.

The results described herein were obtained using high-throughput multitag pyrosequencing to characterize the oral bacteriome and mycobiome of 12 HIV-infected patients and 12 uninfected controls (matched for age, sex, and ethnicity). The number of bacterial and fungal genera respectively ranged between 8 and 14 and 1 and 9 among both uninfected and HIV-infected individuals. The core oral bacteriome (COB) comprised 14 genera in both HIV-infected and uninfected individuals, of which 13 were common to both groups. The core oral mycobiome (COM) which consisted of five genera (with two genera (*Candida* and *Penicillium*) shared between HIV-infected and uninfected individuals), demonstrated a shift in HIV disease. Among *Candida* species, *C. albicans* was the most common (58 percent in uninfected and 83 percent in HIV-infected participants), followed by *C. dubliniensis* (17 percent in both groups). *Pichia*, a fungus present in the COM, was antagonistic to *Candida* (the most common fungal pathogen associated with oral lesions in HIV infection). The mechanism by which *Pichia* antagonized *Candida* involved inhibition of adhesion, germination, and biofilm formation. Accordingly, one embodiment relates to a determination and method that permits an individual to determine, for the first time, that a shift in the COM occurs with HIV-infection, and that *Pichia*, a member of the COM, antagonizes *Candida*, through multiple mechanisms.

Given the above, in one instance, based on the identification of the core oral mycobiome and core oral bacteriome in HIV-infected and uninfected individuals, it is demonstrated that the COM undergoes a shift in HIV-infection. Furthermore, a decrease in abundance of *Pichia* (a harmless yeast present in the COM of uninfected individuals) coincided with increases in *Candida* (which causes oral candidiasis, the most common oral complication of HIV infection) colonization, suggesting an antagonistic relationship between these two fungi. In one embodiment, this antagonism is confirmed by showing that *Pichia* inhibited *Candida*'s ability to adhere, germinate and form biofilms suggesting that modulation of *Candida* virulence factors by *Pichia* is an underlying mechanism. As such, the present invention provides the first confirmation that other fungi present in the same host microenvironment impact *Candida* colonization.

The discovery of an antagonistic interaction between *Pichia* and *Candida* enables one to develop novel approaches (including probiotics) to manage mucosal fungal infections in immunocompromised patients, including those infected with HIV.

In some embodiments, a composition can be provided that includes at least one *Pichia* fungus, or one or more compounds produced therefrom or thereby, to, for example, inhibit the growth and/or reproduction of *Candida*. Compositions of the invention may be selected from, but are not limited to, the group consisting of food products, animal feed, nutritional products, food supplements, food ingredients, health food, oral products, pharmaceutical products and cosmetics. Compositions are also applicable as convenient part or supplement, for example, of the every-day diet or medication. In some embodiments, the composition is a pharmaceutical, food or feed product. In another embodiment, the composition is functional food, i.e., food having any health promoting and/or disease preventing or treating properties. A food product can be selected from the group consisting of dairy products, bakery product, chocolate and confectionary, sugar and gum confectionary, cereal products, snacks, berry or fruit based products and drinks/beverages, including beer. Dairy products include but are not limited to milk, sour milk, yogurts and other fermented milk products, such as cheeses and spreads, milk powders, children's food, baby food, toddler's food, infant formula, juices and soups.

The composition including *Pichia* or one or more compounds produced therefrom may be a pharmaceutical composition and may be used, for example, in solid, semisolid or liquid form, such as in the form of tablets, pills, pellets, capsules, solutions, emulsions or suspensions. Preferably the composition is for oral administration.

In addition to the *Pichia* or one or more compounds produced therefrom, the composition may comprise pharmaceutically or nutritionally acceptable and/or technologically needed carrier(s) (e.g., water, glucose or lactose), adjuvant(s), excipient(s), auxiliary excipient(s), antiseptic(s), stabilizing, thickening or coloring agent(s), perfume(s), binding agent(s), filling agent(s), lubricating agent(s), suspending agent(s), sweetener(s), flavoring agent(s), gelatinizer(s), anti-oxidant(s), preservative(s), buffer(s), pH regulator(s), wetting agent(s), starter(s) or components normally found in corresponding compositions. Any agent, which is not a probiotic may for example be selected from the above-mentioned group. Agents of a composition, e.g. ingredients or components, are either obtained commercially or prepared by conventional techniques known in the art.

In some embodiments, the composition can be formulated as for example, at least one tablet, capsule, pill, mouth wash, toothpaste, chewing gum, lozenge, or powder containing from at least about 5 weight percent to at least about 99 weight percent, at least about 7.5 weight percent to at least about 90 weight percent, or at least about 10 weight percent to at least about 80 weight percent of one or more *Pichia* fungi based on the total weight of the at least one tablet, capsule, pill, mouth wash, toothpaste, chewing gum, lozenge, or powder.

The balance of the composition can include a carrier, such as trehalose, malto-dextrin, nee flour, micro-crystalline cellulose, magnesIUm sterate, inositol, fructooligosaccharide, gluco-oligosaccharide, dextrose, sucrose, talc, water, physiological salt solution, urea, methanol, ethanol, propanol, butanol, ethylene glycol, propylene glycol, white pertrolatum, isopropyl myristate, lanolin, lanolin alcohol, mineral oil, lavender oil, nasturtium extract oil, sorbitan monooleate, cetylstearyl alcohol, hydroxypropyl cellulose, detergent, sucrose stearate, sucrose cocoate, sucrose distearate, 2-ethyl-,1,3-hexanediol, polyoxypropylene-15-stearyl ether, glycerol stearate, glycerin, synthetic spermaceti, cetyl alcohol, butylparaben, propylparaben and methylparaben.

In some embodiments, the composition that includes at least one *Pichia* fungus, or one or more compounds produced therefrom or thereby can be inserted into the oral cavity on a regular basis. For example, a toothpaste embodiment would be used to brush the teeth with a toothbrush, typically at least twice per day. A mouthwash embodiment would be poured into the oral cavity and swished in the mouth for 30-60 seconds. An oral spray, cream or gel embodiment would be sprayed or squirted directly into the mouth. A chewing gum embodiment would be chewed, releasing the ingredients into the mouth. A candy or lozenge embodiment would be inserted into the mouth and sucked on to dissolve the product and deliver the composition to the oral cavity. A dissolvable pill or strip embodiment would be placed in the mouth and held there until the carrier dissolved, thereby releasing the composition into the oral cavity. A powder embodiment could be sprinkled directly into the oral cavity, or added to food.

In some embodiments, the composition can be administered an individual or subject at an amount effective to inhibit the growth and/or reproduction of *Candida* in the oral cavity of an individual. The individual can include healthy and immune-compromised (e.g., HIV-positive individuals.

Example

In this example, we identified the core oral mycobiome (COM) and bacteriome (COB) [present in ≥20% of the subjects] in HIV-infected and uninfected individuals, and demonstrated that the COM undergoes a change in HIV disease. Furthermore, we noted that a decrease in abundance of the yeast *Pichia* coincided with an increase in *Candida* colonization, suggesting an antagonistic relation between these two fungi. We also found that *Candida* growth and modulation of its virulence factors by *Pichia* is a mechanism underlying this interaction. In addition, treatment with *Pichia* Spent Medium (PSM) was efficacious against oral candidiasis when tested in an experimental murine model. Our results provide the first evidence of interaction among members of the oral mycobiome community.

Microbiome Analysis

Oral rinse samples were processed individually using the Fast DNA Spin Kit following manufacturer's instructions (BIO 101; Vista, Calif.). Each extraction tube was agitated three times using a Fast Prep FP120 instrument at a speed setting of 5 for 30 s. Tubes were cooled on ice between agitations. Fungi and bacteria present in these samples were identified with ITS-based and 16S probes, respectively. The ITS1 region from DNA sample extracts was amplified in triplicate using primers with high specificity for ascomycete fungi (fluorescently labeled forward primer ITS1F (CTTG-GTCATTTAGAGGAAGTAA) and unlabeled reverse primer ITS2 (GCTGCGTTCTTCATCGATGC). The ITS primers were selected in this study to detect the presence of various fungi since these primers are able to detect consensus sequences present in a broad range of fungi. For bacterial identification, extracted DNA was amplified by PCR using routinely used universal primers [fluorescently labeled forward primer 27F (5'-6FAM-AGAGTTTGATCCTG-GCTCAG-3') and unlabeled reverse primer 355R5' (5'-GCTGCCTCCCGTAGGAGT-3')], which amplify the first two hyper-variable regions of 16S rRNA and are commonly used for microbiome analysis. Microbiome analysis was performed using multitag 454 pyrosequencing (MTPS) technique, which was used for detailed characterization of nucleic acids.

Strains

The *Candida albicans* (strains 10341, GDH2346), *Pichia* (MRL81), *Penicillium* (MRL22345) and *Cladosporium* (MRL1458) strains tested in this study were obtained from the OHARA Repository at Case and the culture collection of the Center for Medical Mycology. Fungal strains were maintained on Sabouraud dextrose agar (SDA, [yeast extract, peptone, and dextrose at 1:2:1]) (Difco Laboratories, Detroit, Mich.) medium. Since species-level identification of *Pichia* based upon morphological or physiological features alone is usually not possible, we used a molecular approach (based on sequence analysis of the internal transcribed spacer and D1/D2 ribosomal DNA regions) to confirm the identity of *Pichia* MRL81 strain. Our analysis revealed that this strain was *P. farinosa*. All strains were kept at −80° C. for long-term storage.

Biochemical Characterization of *Pichia* Spent Medium (PSM)

The effect of *Pichia* supernatant on *Candida* growth, germination, adherence, biofilm formation, and its biochemical properties was determined as described below.

Effect of *Pichia* Supernatant on *Candida* Growth

To evaluate the effect of *Pichia* supernatant on *Candida* growth, *Pichia* spent medium (PSM) was obtained by centrifuging 100-mL culture of *Pichia* grown in SDB (for 48 h), and filter sterilizing it. Next, *Candida* cells ($1\times10^5$ cells/mL) were incubated with PSM at 35° C. and growth was followed for 48 h. Aliquots were collected at 2 h intervals and *Candida* growth was measured spectrophotometrically at 600 nm.

Germination Assay

Effect of *Pichia* spent media (PSM) on *Candida* germination was determined using *C. albicans* strain SC5314, as described previously. *Candida* cells were grown planktonically in the absence or presence of PSM. Germination rate was compared with that of cells grown in media containing fetal bovine serum (FBS) (Hyclone, Thermo Fisher Scientific, Rockford, Ill.), a known inducer of germination. Briefly, *C. albicans* cells were grown and the cell density was adjusted to $1\times10^7$ cells/mL in Hanks balanced salt solution (HBSS) (Mediatech). In separate 1.5-mL tubes, 50 mL of these cells were diluted to a density of $5\times10^5$ cells/mL in HBSS (blank control), FBS, or PSM, and incubated on a rocker at 37° C. for up to 4 h. At 15-min intervals, 10-μL samples from each media type were microscopically examined using a hemacytometer. Total cell count and germination (defined as a germ-tube length greater than or equal to the blastospore diameter) was determined from an average of 4 observations. One hundred to 200 cells were counted per observation. The assays were discontinued when cells clumped together, due to germination, which made it difficult to count individual cells.

Adhesion Assay

The effect of *Pichia* or *Penicillium* (used as a control) cells or supernatant on *Candida* adherence (using strain *C. albicans* SC5314, a clinical isolate used conventionally in *Candida* adhesion and germination assays) was determined as described earlier. Briefly, standardized suspensions of 50 to 200 cells/mL were added onto silicone elastomer disks for 90 min. Disks were then washed in phosphate-buffered saline (PBS) to remove non-adherent cells and placed in wells of 12-well tissue culture plates (Becton Dickinson, Franklin Lakes, N.J.). Two milliliters of warm (55° C.) liquefied SDA was added per well to completely cover the SE disks and allowed to solidify. Plates were incubated overnight (37° C.), and the number of colonies adhering per disk was counted using a dissecting microscope.

Biofilm Evaluation

The effect of oral fungi (*Pichia, Cladosporium* or *Penicillium*) or their supernatant on the ability of *Candida* to form biofilms was evaluated using metabolic activity assay and confocal microscopy, as described earlier. Briefly, *Candida* cells were incubated in the presence or absence of *Pichia* cells or spent medium (supernatant, PSM) at different relative ratios (1:3, 1:1, 3:1), and allowed to form biofilms for 48 h on silicone elastomer catheter discs. The amount of biofilm formed was assayed colorimetrically using the XTT (2,3-bis (2-methoxy-4-nitro-5-sulfophenyl)-5-[(phenylamino) carbonyl]-2H-tetrazolium hydroxide, Sigma-Aldrich) metabolic activity assay in which XTT is converted by metabolically active cells to a red formazan product. In addition, the effect of fungal supernatants on the morphology and architecture of the formed biofilms was evaluated using confocal scanning laser microscopy (CSLM). Briefly, biofilms were stained with the fluorescently labeled polysaccharide-indicating lectin Concanavalin Alexa Fluor 488 conjugate (CON-A, 25 μg/mL; Invitrogen) and metabolic activity indicator dye FUN1 (10 μM; Invitrogen). After staining, discs containing biofilms were flipped and placed on a 35-mm-diameter glass-bottom petri dish (MatTek Corp., Ashland, Mass.). Stained biofilms were observed with a Zeiss LSM510 confocal scanning laser microscope equipped with argon and HeNe lasers and mounted on a Zeiss Axiovert100 M microscope (Carl Zeis, Inc.). The objective used was a water immersion C-apochromat lens (40×; numerical aperture, 1.2).

In Vivo Model of Oral Candidiasis

Wild-type C57BL/6 mice (purchased from Charles River Laboratories, Wilmington, Mass.) were immunosuppressed with 4 mg of cortisone acetate (Sigma Chemical Co., St. Louis, Mo.) administered subcutaneously on the day before and 1 and 3 days after challenge with *Candida* cells. Mice were given tetracycline hydrochloride (Sigma Chemical Co., St. Louis, Mo.) in their drinking water (0.5 mg/ml), starting the day before infection. On the day of inoculation, mice were anesthetized and light scratches made on the dorsum of the tongue following by the introduction of *C. albicans* GDH ($10^8$ blastospores). The scratches were superficial, limited to the outermost stratum corneum, and did not cause trauma or bleeding. Mice were divided into groups (n=4); treated with *Pichia* supernatant, 100 μl in the oral cavity twice a day, and untreated control. Topical nystatin (widely used clinically to treat oral candidiasis {Pienaar, 2010 #68495}) was used as a comparator. Treatment began on day 4 post inoculation, mice were sacrificed on day 7 and the tongues harvested for enumeration of tissue fungal burden or histopathology with Periodic acid-Schiff stain. Additionally, tongues were visually assessed daily beginning day 1 post infections to assess severity of the infection using the following scoring system: A score of 0 indicates the appearance of a normal tongue, with intact light reflection and no visible signs of infection, a score of 1 denotes isolated patches of fungus, a score of 2 when confluent patches of fungus are observed throughout the oral cavity, and a score of 3 indicates the presence of wide-spread fungal plaques and erosive mucosal lesions.

Identification of PSM as a Protein

Since the antibiofilm activity of PSM was secretory in nature, we determined whether this activity was due to a protein, carbohydrate or small molecule (metabolite). We exposed PSM to proteinase K (which digests most proteins), NaOH (which denatures carbohydrates), or acetonitrile extraction (that isolates metabolites). We also determined the effect of heat on PSM activity by exposing it to 90° C. temperature in a water bath for 10 min. The ability of these differently treated PSM to inhibit *Candida* biofilms was evaluated as above.

Results

Participant Demographics

A total of 24 individuals were enrolled in the study, with 12 HIV-infected patients and 12 uninfected individuals (11 males and one female in both study groups, Table 1). The mean age was 38.7 and 38.8 years in HIV-infected (age range: 22-56) and uninfected (age range: 22-59) groups, respectively. Among the 12 HIV-infected patients, eight had initiated antiretroviral therapy. In both study groups, self-reported ethnicities were: six African-Americans, two Hispanics, and four Caucasians. While all samples were analyzed for fungal microbiota, one of the samples did not provide robust signals for the bacterial microbiome, and hence was excluded from the analysis. In addition, the corresponding matched uninfected control sample was also excluded. As a result, there were 12 uninfected-HIV-infected sample pairs for mycobiome analysis but only 11 sample pairs for bacteriome analysis.

*coccus* and *Rothia* were the most common genera; while in controls the most abundant bacteria were *Prevotella, Streptococcus* and *Fusobacterium*. The core oral bacteriome (COB) consisted of 14 genera in both HIV-infected and uninfected individuals, of which 13 (*Actinomyces, Granulicatella, Fusobacterium, Leptotrichia, Rothia, Neisseria, Haemophilus, Pasteurella, Porphyromonas, Prevotella, Gemella, Streptococcus,* and *Veillonella*) were common to both groups. We found that *Capnocytophaga* was present only in HIV-infected patients while *Aggregatibacter* was present in uninfected individuals only. These results suggest that the COB of HIV-infected patients was similar to that of uninfected individuals with minimal difference.

Oral Mycobiome of HIV-Infected Patients Exhibits Differences from Uninfected Individuals Our results showed that the number of fungal genera present in oral wash samples ranged between 1-9 per person among uninfected and HIV-infected individuals. Among HIV-infected patients, *Candida, Epicoccum,* and *Alternaria* were the most common genera (present in 92%, 33%, and 25%, respectively), while in uninfected participants, the most abundant fungi were *Candida, Pichia,* and *Fusarium* (58%, 33%, and 33%, respectively). The COM of HIV-infected and uninfected individuals consisted of five genera; of these, *Candida* and *Penicillium* were common between the two groups, while differing in the remaining genera

TABLE 1

Demographic information of study participants

| Group | ID | Age (years) | Gender[§] | Ethnicity[*] | CD4 cell count (cells/mm$^3$) | Viral load (U/mL) | Medication |
|---|---|---|---|---|---|---|---|
| HIV-infected | 1 | 31 | M | H (W) | 380 | 158000 | None |
| | 2 | 56 | M | AA | 639 | 75 | Atripla |
| | 3 | 52 | M | AA | 800 | 48 | Atripla |
| | 4 | 40 | M | C (W) | 947 | 48 | Atripla |
| | 5 | 40 | M | C (W) | 280 | 48 | Atripla |
| | 6 | 22 | M | AA | 966 | 1100 | None |
| | 7 | 31 | F | H (W) | 1029 | 48 | Rotanivir, Fosamprenavir, Combivir |
| | 8 | 42 | M | AA | 814 | 53 | Rotanivir, Atazanavir, Truvada |
| | 9 | 22 | M | C (W) | 581 | 115000 | None |
| | 10 | 52 | M | AA | 5 | 185000 | None |
| | 11 | 31 | M | C (W) | 670 | 68 | Atripla |
| | 12 | 45 | M | AA | 899 | 48 | Rotanivir, Atazanavir, Truvada |
| Uninfected | 1C | 34 | M | H (W) | NA | NA | None |
| | 2C | 46 | M | C (W) | NA | NA | None |
| | 3C | 59 | M | AA | NA | NA | None |
| | 4C | 22 | M | C (W) | NA | NA | None |
| | 5C | 37 | M | AA | NA | NA | None |
| | 6C | 34 | F | H (W) | NA | NA | None |
| | 7C | 40 | M | C (W) | NA | NA | None |
| | 8C | 27 | M | C (W) | NA | NA | None |
| | 9C | 53 | M | AA | NA | NA | None |
| | 10C | 44 | M | AA | NA | NA | None |
| | 11C | 22 | M | AA | NA | NA | None |
| | 12C | 47 | M | AA | NA | NA | None |

[§]Gender: M—Male, F—Female.
[*]Self-reported ethnicity: W = White; H = Hispanic; C = Caucasian; AA = African-American Oral Bacteriome of HIV-Infected Participants were Similar to that of Uninfected Individuals Our results showed that the number of bacterial genera in the oral microbiota of study participants ranged between 8-14 per person among HIV-infected and uninfected individuals. Among HIV-infected patients, *Prevotella, Strepto-* demonstrating that the COM of HIV-infected patients differs from that of age- and sex-matched uninfected controls. Among the *Candida* species detected, *C. albicans* was the most common (58% in uninfected and 83% in HIV-infected patients), followed by *C. dubliniensis* (17% in both groups).

Correlation Between Members of the Oral Bacteriome and Mycobiome in HIV-Infected Patients Next, we determined how the individual members of the oral bacteriome and mycobiome are correlated within their respective communities, and also across the two communities. We grouped the microbiome abundance data into independent mycobiome and bacteriome data matrices and conducted correlation analysis using R statistical computing software. We found 15 bacteria-fungi pairs that were correlated significantly in samples from non-infected study participants (Table 2). Among these significant correlation pairs, two pairs (*Rothia-Cladosporium* and *Granulicatella-Cryptococcus*) were negatively correlated (coefficient −0.61 and −0.65, respectively). The remaining 13 pairs of significantly correlated pairs exhibited positive correlation with coefficients ranging from 0.64 (*Aggregatibacter-Lactarius*) to 0.86 (*Capnocytophaga-Cladosporium*). In comparison, there were 12 statistically significant bacteria-fungi pairs in HIV-infected patients, with 11 positive (coefficient of 0.64 for 8, 0.74 for two pairs, Table 2) and one with negative correlation (*Campylobacter-Candida*, coefficient −0.67).

*Pichia* Inhibits the Ability of *C. albicans* to Form Biofilms

Figure 4:
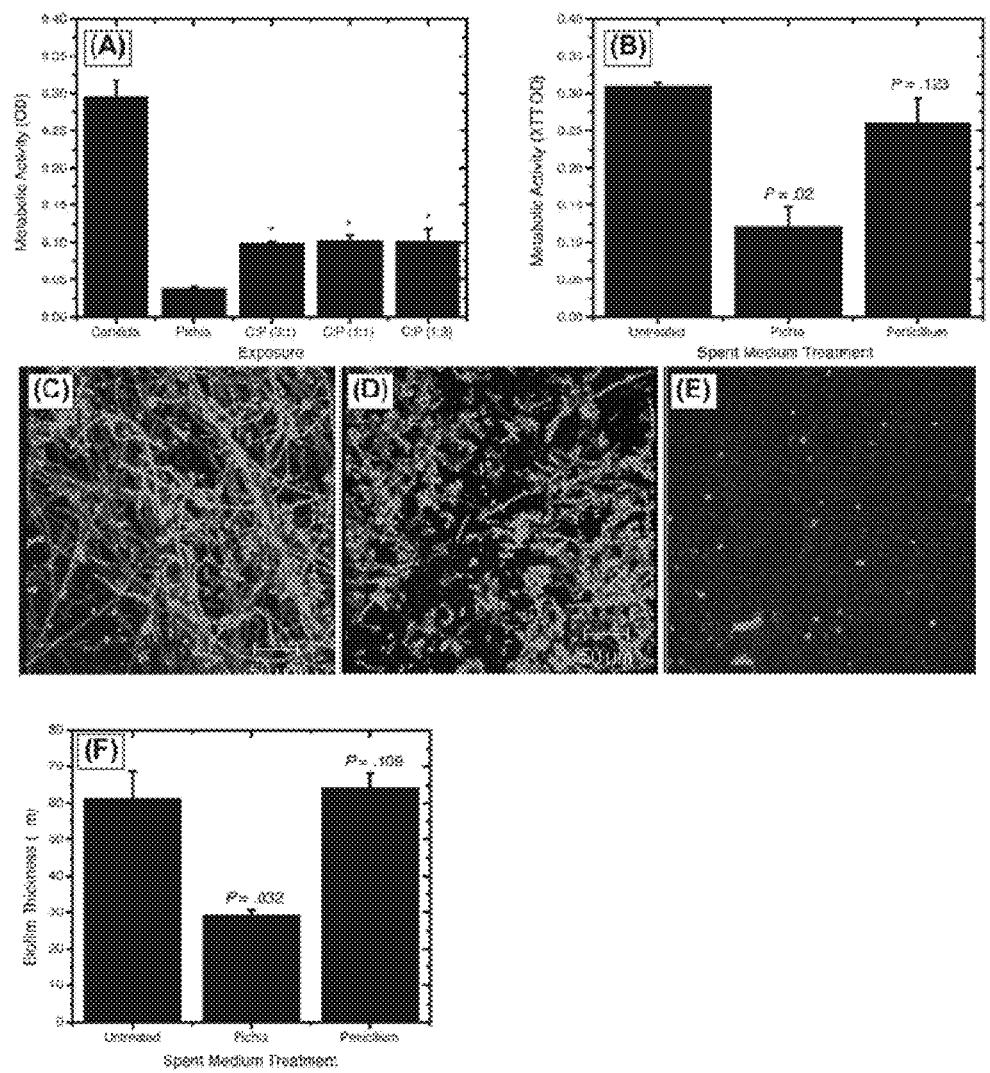
FIGS. 4(A-F) illustrates graphs and images showing the activity of *Pichia* spent medium (PSM) against fungal biofilms.

Co-incubation of *C. albicans* with *Pichia* cells at different ratios (*Candida:Pichia*::3:1, 1:1, or 1:3) resulted in significant inhibition of biofilm formation at all ratios tested (FIG. 4A, P<0.05). Moreover, there was no significant difference in the extent of biofilm inhibition between the different cell densities of *Pichia* examined. These results demonstrated that *Pichia* cells exhibited an inhibitory effect on *Candida* biofilms.

Next, to determine whether the biofilm-inhibitory activity of *P. farinosa* was mediated by secretory factor/s, we determined the effect of spent medium (supernatant) of this yeast on *C. albicans* biofilms using a metabolic activity (XTT) assay described earlier. Spent medium from *Penicillium* was used as a control since this fungus had the same abundance in HIV-infected and uninfected individuals (present in 25% of samples in each group). Our data showed that the metabolic activity of *Candida* biofilms treated with *Pichia* spent

TABLE 2

Correlation between bacteriome and mycobiome in uninfected and HIV-infected study participants

| Uninfected Individuals | | | | HIV-Infected Patients | | | |
|---|---|---|---|---|---|---|---|
| Bacteria | Fungi | P-value | Correlation | Bacteria | Fungi | P-value | Correlation |
| *Atopobium* | *Antarctic* | 0.009 | 0.74 | *Megasphaera* | *Aspergillus* | 0.009 | 0.74 |
| *Capnocytophaga* | *Cladosporium* | 0.001 | 0.86 | *Campylobacter* | *Candida* | 0.023 | −0.67 |
| *Rothia* | *Cladosporium* | 0.021 | 0.68 | *Megasphaera* | *Clavispora* | 0.009 | 0.74 |
| *Oribacterium* | *Cryptococcus* | 0.009 | 0.74 | *Eubacterium* | *Epicoccum* | 0.035 | 0.64 |
| *Rothia* | *Cryptococcus* | 0.048 | −0.61 | *Parvimonas* | *Epicoccum* | 0.035 | 0.64 |
| *Capnocytophaga* | *Emericella* | 0.009 | 0.74 | *Paludibacter* | *Epicoccum* | 0.035 | 0.64 |
| *Granulicatella* | *Epicoccum* | 0.025 | 0.67 | *Tannerella* | *Epicoccum* | 0.035 | 0.64 |
| *Pasteurella* | *Epicoccum* | 0.012 | 0.72 | *Capnocytophaga* | *Rhodotorula* | 0.035 | 0.64 |
| *Atopobium* | *Exophiala* | 0.009 | 0.74 | *Eubacterium* | *Trichosporon* | 0.035 | 0.64 |
| *Capnocytophaga* | *Hanseniaspora* | 0.009 | 0.74 | *Parvimonas* | *Trichosporon* | 0.035 | 0.64 |
| *Capnocytophaga* | *Kodamaea* | 0.009 | 0.74 | *Paludibacter* | *Trichosporon* | 0.035 | 0.64 |
| *Aggregatibacter* | *Lactarius* | 0.035 | 0.64 | *Tannerella* | *Trichosporon* | 0.035 | 0.64 |
| *Granulicatella* | *Pichia* | 0.031 | −0.65 | | | | |
| *Sneathia* | *Rhodotorula* | 0.009 | 0.74 | | | | |
| *Atopobium* | *Trichosporon* | 0.009 | 0.74 | | | | |

*Pichia*, a Member of the Core Oral Mycobiome, Exhibits Antagonism Against *Candida*

Having defined the core mycobiome, next we investigated whether members of the core oral mycobiome are associated with *Candida*, the most common oral fungal pathogen of HIV-infection. We found that decrease in *Pichia* abundance coincided with an increase in *Candida* colonization (FIG. 3A), suggesting antagonism between *Pichia* and *Candida*. This striking observation necessitated further testing to confirm whether *Pichia* exert direct effect on *Candida* and to characterize the mechanism by which this interaction is affected.

*Pichia* Inhibits Growth of *Candida*, *Aspergillus* and *Fusarium*

Figure 3:
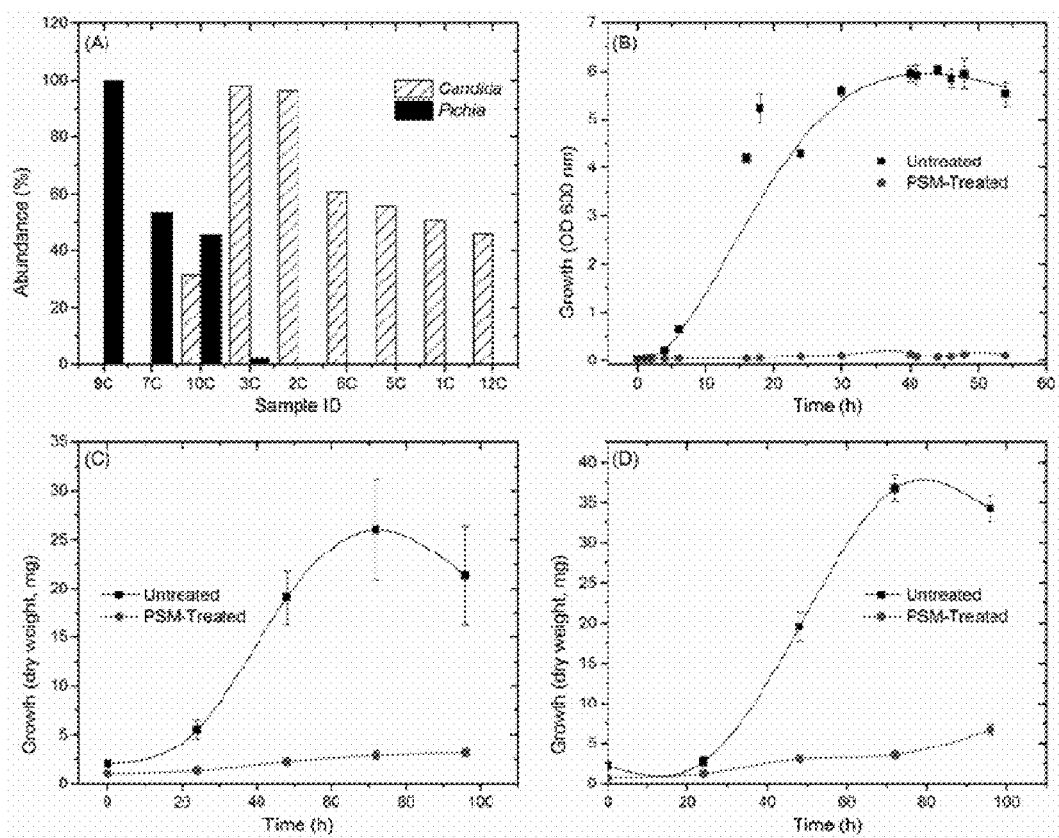
FIGS. 3(A-D) illustrate graphs showing antagonistic relation between *Pichia* and other fungi, where

Next, we investigated the ability of *Pichia* to inhibit growth of *C. albicans*, by allowing blastospores to grow in the presence or absence of *Pichia* spent medium (PSM). As shown in FIG. 3B, PSM completely inhibited *Candida* growth, demonstrating a direct inhibitory effect of *Pichia* against *Candida*. We also assessed the effect of PSM on growth of *Aspergillus* and *Fusarium* by determining their dry weight. As shown in FIGS. 3C and D, *Aspergillus* and *Fusarium* were unable to exhibit growth in presence of PSM. These studies demonstrated that PSM exhibits broad-spectrum activity against pathogenic fungi.

medium (PSM) was significantly reduced compared to untreated and *Penicillium*-treated controls (FIG. 5B, P<0.05). Additionally, spent medium from *Cladosporium* (which, like *Pichia*, was present only in uninfected individuals) had no effect on *Candida* biofilms (P>0.05, data not shown), proving that the anti-*Candida* activity was *Pichia*-specific. We used confocal laser scanning microscopy (CLSM) to determine the effect of PSM on *C. albicans* biofilm architecture. While untreated and *Penicillium*-treated *Candida* formed robust biofilms (FIG. 4C-D), exposure to PSM resulted in disrupted biofilms, with sparse yeast cells and no extracellular matrix or hyphae observed (FIG. 4E). Moreover, thickness of *Candida* biofilms exposed to PSM was significantly reduced compared to that of controls (FIG. 5F, P<0.05).

*Pichia* Inhibits *Candida* Adherence and Germination

Since adhesion and germination are key steps in mature *Candida* biofilm formation and are known *Candida* virulence factors, we examined whether *P. farinosa* spent medium affects these processes. Our data showed that the number of adherent colony forming units (CFUs) in cells treated with *Pichia* supernatant was significantly lower than untreated *Candida* cells (3.0±2.5 vs. 50±25.9 CFUs, respectively, P<0.003). Moreover, *C. albicans* cells exposed to *Pichia* supernatant formed stunted germ tubes (FIG. 5A-B) indicating that a secreted component of *Pichia* inhibits *Candida* germination.

PSM is Effective Against Oral Candidiasis in an Experimental Murine Model

To determine whether the in vitro activity of PSM against *Candida* is also exhibited in vivo, we evaluated the efficacy of PSM in an experimental murine model of oral candidiasis. We found that compared to the untreated mice, the clinical score of PSM-treated mice was significant reduced compared to untreated mice by day 7 (P=0.011, FIG. 6A). The fungal burden of tongue from PSM-treated mice was also significantly reduced compared to untreated controls (P=0.04, FIG. 6B). Histological examination showed extensive tissue invasion by fungal hyphae and destruction of the epithelium in untreated controls (FIG. 6C). In contrast, tongue epithelium in PSM-treated mice revealed only superficial hyphal invasion and intact tissue structures (FIG. 6D). In general, nystatin exhibited sub-optimal efficacy based on clinical score (FIG. 6A), tissue burden (FIG. 6B), and histology, where extensive hyphal invasion was observed (FIG. 6E). These results demonstrated that PSM was efficacious against oral candidiasis in vivo when tested in an experimental oral model of candidiasis.

Having described the invention, the following is claimed is:

1. A method for reducing the amount of *Candida* in the oral cavity of an individual in need thereof comprising administering to said individual a composition that includes *Pichia farinosa* fungus at an amount effective to inhibit the growth and/or reproduction of *Candida* in the oral cavity of the individual, wherein the composition is free of other fungi besides *Pichia farinosa*.

2. The method of claim 1, wherein the method involves administering at least one tablet, capsule or pill containing from at least about 5 weight percent to at least about 99 weight percent of *Pichia farinosa* fungi based on the total weight of the at least one tablet, capsule or pill.

3. The method of claim 1, wherein the method involves administering at least one tablet, capsule or pill containing from at least about 7.5 weight percent to at least about 90 weight percent of *Pichia farinosa* fungi based on the total weight of the at least one tablet, capsule or pill.

4. The method of claim 1, wherein the method involves administering at least one tablet, capsule or pill containing from at least about 10 weight percent to at least about 80 weight percent of *Pichia farinosa* fungi based on the total weight of the at least one tablet, capsule or pill.

* * * * *